United States Patent [19]

Szafranski et al.

[11] Patent Number: 5,679,533

[45] Date of Patent: Oct. 21, 1997

[54] BIOTIN-BINDING CONTAINMENT SYSTEMS

[75] Inventors: Przemyslaw Szafranski, Boston; Charlene M. Mello, Rochester; Takeshi Sano, Boston, all of Mass.; Kenneth A. Marx, Francestown, N.H.; Charles R. Cantor, Boston, Mass.; David L. Kaplan, Stow, Mass.; Cassandra L. Smith, Boston, Mass.

[73] Assignees: Trustees of Boston University, Boston, Mass.; The United States of America as Represented by the Secretary of the Army, Washington, D.C.

[21] Appl. No.: 479,390

[22] Filed: Jun. 7, 1995

Related U.S. Application Data

[63] Continuation of Ser. No. 432,017, May 1, 1995.
[51] Int. Cl.$^6$ .................................................. G01N 33/53
[52] U.S. Cl. .................. 435/72; 435/7.32; 435/7.37; 435/172.3; 435/262; 435/262.5; 435/320.1
[58] Field of Search ......................... 435/172.3, 320.1, 435/252.3, 4, 7.1, 7.32, 7.37, 7.5, 262, 262.5, 7.2; 935/59, 62, 72, 41, 43

[56] References Cited

FOREIGN PATENT DOCUMENTS

WO94/00992  1/1984  WIPO ........................ A01N 63/02

OTHER PUBLICATIONS

Sano et al., "Expression of a cloned streptavidin gene in Escherichia coli", Proc. Nat. Acad. Sci. USA, 87: 142–146 Jan. 1990.

Molin et al., "Suicidal genetic elements and their use in biological containment", Annu. Rev. Microbiol. 47: 139–166 1993.

Primary Examiner—James Ketter
Assistant Examiner—Ivem Yucel
Attorney, Agent, or Firm—James Remenick; Baker & Botts, L.L.P.

[57] ABSTRACT

The present invention relates to genetic containment systems which express a biotin-binding component that can be used for selectively destroying recombinant cells such as genetically engineered microorganisms. These systems may comprise a streptavidin or an avidin gene whose expression is controlled by a regulatable promoter. The regulatory agent such as a transcriptional effector is expressed from another gene which may also be expressed and its expression controlled by the containment system. Expression of the agent can be designed to respond to physiological changes in the environment. The invention also relates to containment systems and methods for the selective detection or tracking of recombinant cells and to eukaryotic and prokaryotic cells which contain these genetic containment systems.

21 Claims, 3 Drawing Sheets

BIOTIN-BINDING CONTAINMENT SYSTEMS

This application is a continuation of application Ser. No. 08/432,017, filed May 1, 1995.

RIGHTS IN THE INVENTION

This invention was made with United States Government support, under grant number DAAH04-94-2-0004, awarded from the United States Department of the Army, and the United States government has certain rights in the invention.

BACKGROUND

1. Field of the Invention

This invention relates to genetic systems for the containment of recombinant organisms and to cells which possess these systems. The invention also relates to methods for the selective detection and selective destruction of recombinant cells.

2. Description of the Background

Genetic engineering, although still in its infancy, is increasingly being utilized in medicine, agriculture and industry. Genetically engineered microorganisms (GEMs), microorganisms which have deliberately had their genetic character in some way directly altered, are among the most common tools for the genetic engineer. These microorganisms, which may be prokaryotic or eukaryotic or unicellular or multicellular, are used in the generation of, for example, medical products, insect-resistant crops and healthier food products. GEMs are also widely used in the elimination of waste products such as biomass, sludge and accidental spills of oil or toxins.

Surprisingly, little data is available on how GEMs survive in the environment or how recombinant DNA can spread among indigenous bacterial populations. It is relatively unknown whether recombinant microorganisms have the ability to alter, in a temporary or permanent fashion, a natural ecosystem or any environment which they might be found. Considering the undetermined consequences associated with the release of new genetic material into the environment, various techniques have been developed in an effort to destroy GEMs on demand.

As microorganisms are generally biodegradable, when killed, they pose little risk of damage to the environment. Typically, GEMs are killed and disposed of through physical or chemical means such as incineration, glassification, solvent extraction, chemical treatments, super critical fluid extraction, ozonolysis, UV light treatments and many others. These methods are generally expensive and time consuming requiring a great deal of labor and physical manipulations. Even incineration is coming under increasing scrutiny due to concerns with gaseous outputs. In general, the costs for any of these methods runs in the hundreds to the thousands of dollars per ton of contaminated material due to the hazardous nature of the material, handling issues, residue problems after treatment, energy input costs and related issues.

Although these techniques are quite effective, each is based on the principle that the GEMs can be physically confined. However, absolute confinement is often not possible or simply impractical. More recent techniques have focused on various methods of biological containment. Potential risks associated with deliberate or unintentional release of GEMs are minimized by the use of debilitated mutant strains or non-conjugative, non-mobilized plasmids. GEMs that escape physical confinement, according to a preprogrammed genetic design, are destroyed or cannot successfully reproduce. For example, GEMs can be engineered to require an essential nutrient which is otherwise rare or non-existent in the natural environment. GEMs can also be programmed to die in the presence of compounds which are abundant outside of the laboratory setting. Additional approaches include the introduction of conditional maintenance functions into GEMs, so that their survival is dependent on the specific environments (J. L. Ramos et al., Bio/Technology 13:35–37, 1995) or growth phase (P. Klemm et al., Appl. Environ. Microbiol. 61:481–86, 1995). Thus, by inserting toxic genes transcribed from promoters responding to environmental or intracellular changes, the viability of GEMs can be controlled. Unfortunately, the overall efficiency of suicide systems typically becomes reduced over time by mutational inactivation of the lethal cassettes although some systems benefited by combining two or more different lethal genes.

The most extensively studied toxic genes represent the *Escherichia coli gef* gene family (*hok, gef* and *relF*), whose expression disrupts the cell membrane potential (A. K. Bej et al., Appl. Environ. Microbiol. 54:2472–77, 1988). Other successfully tested genes include *Serratia marcescens* and *Staphylococcus aureus* endonucleases (S. Molin, Curr. Op. Biotech. 4:299–305, 1993), *Serratia liquefaciens* phospholipase A (S. Molin et al., Annu. Rev. Microbiol. 47:139–66, 1993), and *Bacillus subtilis sacB* gene which confers sucrose sensitivity (G. C. Recorbet et al., Appl. Environ. Microbiol. 59:1361–66, 1993). Preliminary experiments with lysis genes from bacteriophages are also promising (S. Molin et al., Annu. Rev. Microbiol. 47:139–66, 1993).

Prior studies to control the proliferation of genetically engineered microorganisms have primarily considered two basic approaches. The first approach was to use no containment system at all for the engineered microorganism. The assumption was that even if the engineered organisms survive, they would not disrupt normal ecological balances in the environment. The other approach was to develop suicide cassettes to control the survival of the genetically engineered microorganism. Variations include the induction of peptides to disrupt membrane integrity (A. K. Bej et al., Appl. Environ. Microbiol. 54:2472–77, 1988), a TOL plasmid suicide system involving induction of the *gef* gene to promote cell death (A. Contreras et al., Appl. Environ. Microbiol. 57:1504–8, 1991; S. Molin et al., Bio/Technology 5:1315–18, 1987) and induction of a *relF* gene to promote cell suicide. However, with these approaches, the levels of inducers and the formation of resistance clones due to high mutation rates, genetic instability, remain as problems.

SUMMARY OF THE INVENTION

The invention overcomes the problems and disadvantages associated with current strategies and designs and provides novel genetic systems, genetic elements and methods for selectively killing or detecting recombinant organisms.

One embodiment of the invention is directed to genetic containment systems comprising a suicide cassette that encodes a biotin-binding component. The biotin-binding component, which may be streptavidin, avid or a modification of these proteins, can be either the suicide gene or a marker gene.

Another embodiment of the invention is directed to nucleic acids that encode genetic containment systems comprised of a gene encoding a biotin-binding product whose expression is controlled by a transcriptional effector also encoded within the nucleic acid. Nucleic acids may be suicide cassettes wherein the suicide gene encodes a streptavidin or avidin protein, or a conventional suicide gene.

Another embodiment of the invention is directed to cells which contain genetic containment systems that encode a biotin-binding component. Cells may be prokaryotic such as a bacterial cell or eukaryotic such as a plant, animal or yeast cell.

Another embodiment of the invention is directed to method for selectively killing a recombinant microorganism. The microorganism is transformed with a nucleic acid which contains a suicide cassette that encodes a biotin-binding protein such as streptavidin. The cell can be killed by stimulation of streptavidin which binds and effectively eliminates biotin from the cell.

Another embodiment of the invention is directed to methods for the specific detection of recombinant cells. Cells are transformed with a nucleic acid containing a genetic containment system which encodes a biotin-binding protein. Expression of the cassette can be coupled with expression of the biotin-binding protein. Cells can be contacted with a biotinylated solid support and thereby detected.

Other embodiments and advantages of the invention are set forth, in part, in the description which follows and, in part, will be obvious from this description and may be learned from the practice of the invention.

DESCRIPTION OF THE INVENTION

As embodied and broadly described herein, the present invention is directed to biotin-binding genetic containment systems and to recombinant cells which contain these systems. The invention is also directed to methods for the detection and selective destruction of recombinant cells using biotin-binding expression systems.

With the advent of recombinant technology, GEMs, or genetically engineered microorganisms, are being used with ever increasing frequency in a wide array of industrial technologies. Although most pose little direct concern to the environment or humans, there still exists the possibility of a unpredicted and detrimental consequence resulting from the release of new genetic material into the natural environment. Conventional safety procedures include physical confinement and subsequent sterilization of all materials associated with the GEMs, or the incorporation of suicide cassettes into the microorganisms. Unfortunately, physical confinement procedures, when possible, are expensive and time consuming and generally are not applicable to actual conditions. Further, available genetic containment systems are genetically unstable or do not operate successfully in the complex conditions encountered in the natural environment. These suicide systems often cannot be adapted to specific cells or the specific environmental conditions being utilized.

The present invention overcomes these and other problems by providing a genetic containment system based on the expression of a biotin-binding component such as streptavidin, avidin or another biotin-binding gene expression product. Streptavidin and avidin are each fairly toxic in most cellular systems. Toxicity is caused by their exceptionally high binding affinity for biotin, an essential element for a very wide variety of microorganisms including bacteria, plant and animal cells, and even yeast cells. Binding effectively depletes this basic vitamin from the cell and kills the host organism or microorganism. The system is, thus, broadly applicable across class, order, genus and species boundaries, and can be used in most situations irrespective of physiological conditions in the laboratory or the natural environment. As such, biotin-binding genetic containment systems are useful to restrict the proliferation of GEMs as well as other microorganisms and organisms in general.

Streptavidin, the preferred biotin-binding component, is a tetrameric protein, having four identical subunits, and is secreted by the actinobacterium *Streptomyces avidinii*. Both streptavidin, and its functional homolog avidin, exhibit extremely tight and highly specific binding to biotin which is one of the strongest known non-covalent interactions ($K_d \sim 10^{-15}$M) between proteins and ligands. Although avidin and streptavidin have almost the same high affinity for biotin, they are different in many other respects. The two proteins have different molecular weights, electrophoretic mobilities and overall amino acid composition. Avidin is a glycoprotein found in egg whites and the tissues of birds, reptiles and amphibia. Like streptavidin, avidin has almost the same high affinity for biotin and exists as a tetramer with a molecular weight of between about 67,000 to about 68,000 daltons. Avidin also has a high isoelectric point of between about 10 to about 10.5 and contains carbohydrates which cause it to bind non-specifically to biological materials including cell nuclei, nucleic acids and lectins. These non-specific interactions make avidin less suitable than streptavidin for many applications.

The full-length streptavidin monomer is 159 amino acids in length, some 30 residues longer than avidin. It contains no carbohydrate and has a slightly acidic isoelectric point of about 6.0 which accounts, in part, for the low non-specific binding level. Each subunit of streptavidin is initially synthesized as a precursor of 18,000 daltons which forms a tetramer of about 75,000 daltons. Secretion and post-secretory processing results in mature subunits having an apparent size of 14,000 daltons. Processing occurs at both the amino and carboxyl termini to produce a core protein of about 13,500 daltons, having about 125 to 127 amino acids. This core streptavidin forms tetramers and binds to biotin as efficiently as natural streptavidin. The mature streptavidin tetramer binds one molecule of biotin per subunit and the complex, once formed, is unaffected by most extremes of pH, organic solvents and denaturing conditions. Separation of streptavidin from biotin requires conditions, such as 8M guanidine, pH 1.5, or autoclaving at 121° C. for 10 minutes. Mutations of the streptavidin or core streptavidin protein exist whereby binding affinity is reduced such that dissociation can be more easily performed without damage to the attached biotin-bound molecule.

Biotin, also known as vitamin H or cis-hexahydro-2-oxo-1H-thieno-(3,4)-imidazole-4-pentanoic acid, is a basic vitamin which is essential for most organisms including bacteria and yeast. Its depletion caused by the production of streptavidin in cells is potentially lethal. In mammals, the tissues having the highest amounts of biotin are the liver, kidney and pancreas. Biotin levels also tend to be raised in tumors and tumor cells. In addition to cells, biotin can be isolated from secretions such as milk which has a fairly high biotin content. Biotin has a molecular weight of about 244 daltons, much lower than its binding partners avidin and streptavidin. Biotin is also an enzyme cofactor of pyruvate carboxylase, trans-carboxylase, acetyl-CoA-carboxylase and beta-methylcrotonyl-CoA carboxylase which together carboxylate a wide variety of substrates.

A biotin-binding genetic containment system has numerous advantages over more conventional approaches. First, the system is based on a different suicide function than those previously utilized, namely biotin-binding. Second, the cassette approach described can be used in a wide range of hosts including bacteria, fungi, algae, higher plants and animal cells. Third, rates of mutation appear to be significantly lower than most of those previously reported for other suicide gene and, therefore, there is better control in environmental settings. Fourth, the suicide cassette can be easily coupled to catabolic plasmids to demonstrate function. Consequently, genetic constructs tightly couple the degradation of hazardous chemicals to cell survival. Further, the engineered organisms can be easily detected and monitored with biotin-bound conjugates due to the production of streptavidin.

One embodiment of the invention is directed to a genetic containment system containing at least one nucleic acid cassette that encodes a biotin-binding component. The component may be used as the suicide function or as a marker for subsequent detection of recombinant organisms. The biotin-binding component is preferably a protein which specifically binds to biotin such as streptavidin or avidin, derivatives or mutations of streptavidin or avidin, or combinations of these components. Biotin-binding components may also be nucleic acids such as RNA, DNA or even PNA sequences that have an affinity for biotin and can be expressed or otherwise obtained from nucleic acid.

Genetic containment systems of the present invention contain one or more suicide genes for the pre-programmed death of the recombinant cell. Suicide genes can be conventional genes such as members of the *E. coli gef* gene including *hok, gef* and *relF,* the *Serratia marcescens* and *Staphylococcus aureus* endonuclease genes, the *Serratia liquefaciens* phospholipase A gene, the *Bacillus subtilis sacB* gene, lysis genes from bacteriophages, streptavidin genes, avidin genes, or mutations or combinations of these genes. The biotin-binding aspect may therefore be the principle killing function of the system or an ancillary or secondary feature to supplement another killing function. Consequently, another aspect of the invention is directed to combinations of the biotin-binding containment system with other types of suicide gene cassettes to further extend the killing efficiency of a containment system by reducing mutation rates.

Figure 1:
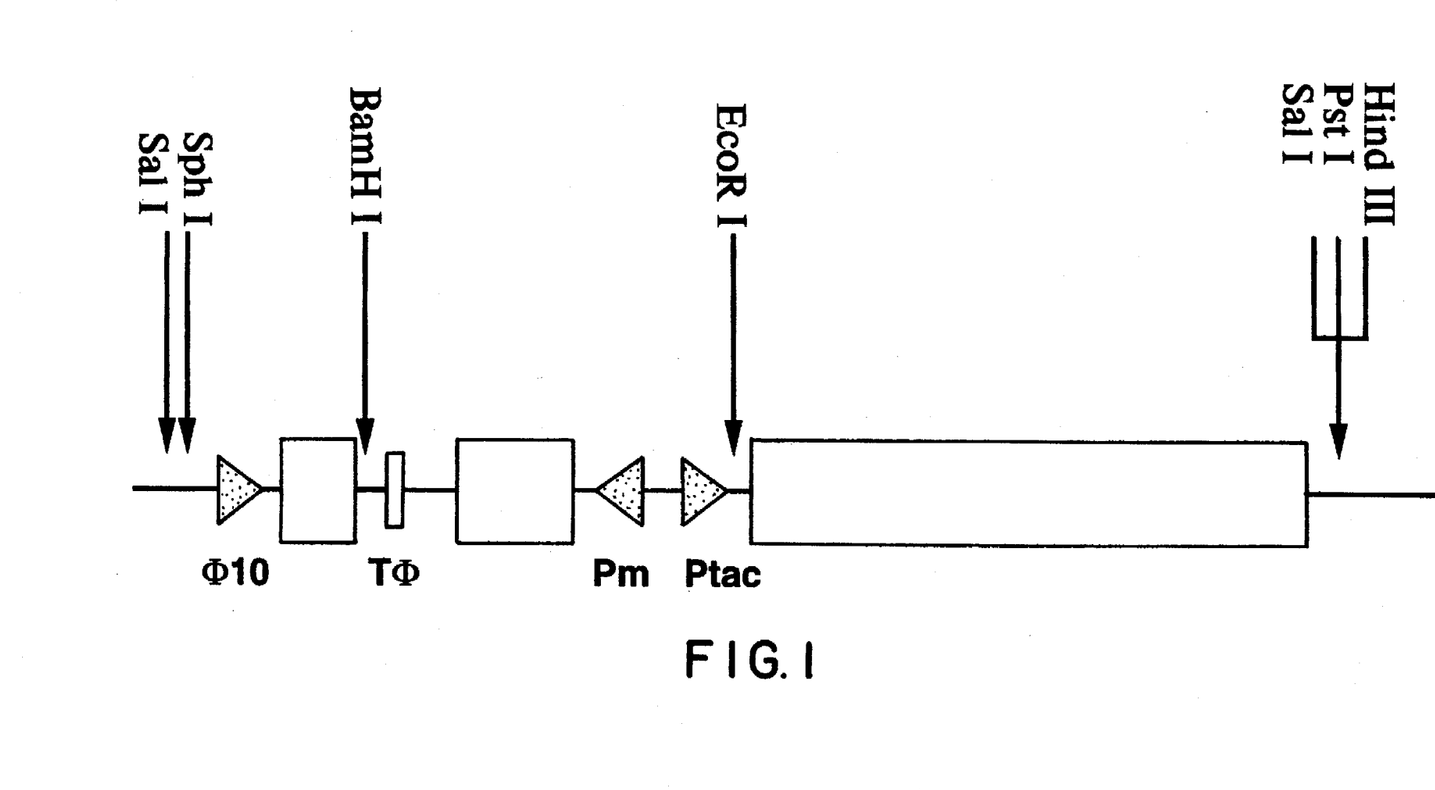
FIG. 1 Physical map of stv cassette.

The need for new killing genes involved in regulatory circuits of programmed cell death comes from imperfect killing by one toxin operating alone. Combinations of at least two different toxic peptides can drop appearance of mutants to $10^{-10}$ and below. For example, the stv-based system shown in FIG. 1, built in the pRO1614 vector (pMB1 and pRO1600 replicon), can deliver a second suicide function in constructs already integrated within chromosome or based on R300B plasmid replicon. This could be performed in *P. putida*. Streptavidin fulfills all requirements of a toxin to be involved in killing systems. The rate of mutational inactivation of stv cassette is at least equal to those estimated for constructs based on a single copy gene per plasmid. Accumulation of mutants, for example with *P. putida*, occurs through insufficient repression of the uninduced system because of extremely low production of LacI protein.

In genetic containment systems, expression of the suicide gene should be tightly controlled. Unwanted generation of the suicide product can have premature deadly consequences. In such situations, the system becomes difficult to replicate and handle in microorganisms and eventually useless for genetic containment. In addition, viable mutations not only develop, but are naturally selected for in every round of reproduction. Expression of the biotin-binding protein can be controlled by functionally linking the gene to a regulatable transcriptional promoter, many of which are well-known to those of ordinary skill in the art. The regulated promoter is preferably a heterologous promoter wherein one or more of the key regulatory agents of the promoter are absent from the host cell. In this fashion, those agents can be introduced artificially and specifically targeted to stimulate or shut down the promoter. Promoters which are useful include the bacteriophage promoters, SP6, T7, T3 and the $\lambda p_L$ promoters, the amino acid promoters *trp, lac,* hybrid *trp-lac, phoA* and *gal,* and the eukaryotic promoters for metallothionein promoters, MMTV promoters, inducible promoters and hybrids and combinations of these promoters. In addition, variations of these promoter sequences can be used in prokaryotic or eukaryotic genetic elements to regulate expression.

Streptavidin-based containment systems represent just one construct of many that can be utilized. There are a wide range of catabolic plasmids available such as NAH, OCT and TOL, and other genes such as lignin peroxidases that degrade specific classes of hazardous organic compounds, and many additional genes that are useful as suicide cassettes. These can be combined with the subject system in a matrix of ways to build a wide range of metabolic capabilities into these organisms to handle a wide range of environmental contamination problems.

As in most genetic containment systems, it is preferable to include another second gene in the system and often in the nucleic acid cassette along with the suicide gene. The gene product for this second gene exercises control over the suicide gene, typically at the transcriptional level, but sometimes at the translational level. In this manner, there is increased control over expression of the suicide gene and a smaller chance of generating mutations which would render the system non-functional. Examples of gene products which can tightly control expression are well-known to those of ordinary skill in the art. To form a genetic containment system, it is preferred that this second gene be made to respond to specific physiological conditions of the cellular environment to stimulate cell killing. Consequently, the expression product of this gene may be subject to a transcriptional or translational effector such as an activator or a repressor, a substrate analog, an enzyme such as an RNA polymerase or another enzyme that is specific to expression or repression of the suicide gene.

Regulatable promoters which respond to changed physiological conditions are well-known and include inducible promoters such as a phage inducible promoters, pH inducible promoters, nutrient inducible promoters (inducible by specific sugars or amino acids), temperature inducible promoter (inducible with heat or cold), radiation inducible promoters (inducible with UVA, UVB, visible light or infrared light), metal inducible promoters (metallothionein inducible), hormone inducible promoters (glucocorticoid inducible), steroid inducible promoters (e.g. the MMTV promoter), and hybrids and combinations of these promoters. Other useful promoters include promoters which respond to the concentration of, or simply the presence or absence of, one or more extrinsic agents in the system. Useful extrinsic and intrinsic agents include substrates or products of amino acid synthesizing enzymes, nucleic acid and nucleotide synthesizing enzymes and most components of bacterial catabolic and anabolic pathway operons. Promoters of this group of genes respond to the presence or absence of amino acids, amino acid analogs, saccharides (e.g. lactose and its analog IPTG), polysaccharides, nucleic acids and nucleotides, and nucleic acid base constituents (e.g. purine and pyrimidine salvage pathway substrates and enzymes). Additional extrinsic or intrinsic agents which are known in either prokaryotes or eukaryotes include hormones, transcriptional activators and repressors, cytokines, toxins, petroleum-based compounds, metal containing compounds, salts, ions, enzyme substrate analogs and derivatives and combinations of these agents.

Optionally, to exercise additional control over the suicide gene, a genetic containment system of the invention may also contain a gene which expresses an inhibitor of the transcriptional effector. Inhibitors are preferably expressed at very low levels in the recombinant cell such that any leakiness of the suicide promoter does not destroy the cell, but is immediately scavenged and inhibited by the constant presence of inhibitor substances. For example, T7 lysozyme is an excellent inhibitor of most T7 RNA polymerases and thereby prevent any T7 RNA polymerase activity. Other inhibitor substances include substrate analogs, competing enzymes and the like. Low levels of expression of this substance is not harmful to most cells and will prevent suicidal events from occurring prematurely. Preferably, the inhibitor is present or is introduced into recombinant cells and expressed constituitively.

One preferred example of a streptavidin-based biological containment system is comprised of a streptavidin gene whose expression is controlled by a first transcription promoter linked to the streptavidin gene. The streptavidin promoter is regulated by a heterologous product which is expressed from another gene which has a different transcriptional promoter linked to the gene. This second transcriptional promoter is inducible by an extrinsic or intrinsic agent added to or removed from the culture. The streptavidin gene may encode the entire mature protein of streptavidin or it may comprise only a core sequence. The amino add sequence may be entirely homologous to the wild type streptavidin or comprise point, deletion or other mutations convenient for the process such as, for example, mutations that alter the affinity of biotin binding.

The regulatable promoter which is attached to the streptavidin gene may be any transcriptional promoter whose activity can be controlled by a heterologous product. Heterologous products are expression products which are not normally present within the cell containing the system. Examples of various types of regulatable promoters include bacteriophage promoters. Most of the T7 RNA polymerase enzyme promoters will only be recognized by T7 RNA polymerase. As most cells do not possess T7 RNA polymerase, only by introduction of the gene which encodes this polymerase can the streptavidin promoter be recognized and the streptavidin protein expressed.

Another embodiment of the invention is directed to a nucleic acid that contains a suicide cassette which encodes a biotin-binding protein. The biotin-binding protein is preferably streptavidin and is utilized for either a suicide function or as a detection marker. The cassette may be a single nucleic acid fragment or the components of the cassette may be distributed on multiple fragments. Preferably, the nucleic acid contain convenient restriction endonuclease sites to simplify transfer of the cassette between vectors, origins of replication for maintenance, transcriptional promoters as described above to control gene expression and recognition sites for various enzymes to maximize expression when stimulated such as during transcription or translation. Useful vectors for carrying or transferring the cassette include viral vectors for eukaryotic cells (AdV, AAV, HSV), plasmids and phage vectors for bacterial cells, and shuttle vectors such as cosmids for both. Optionally, the nucleic acid cassette may also encode inhibitors of the transcriptional effector which can be utilized to reduce the chances of undesired low levels of suicide gene expression. These inhibitors may be expressed at high or low levels, depending on their effect of the host cell and the ability of the suicide gene product to quickly and efficiently overcome the inhibition upon expression. Preferably, the inhibitor is constituitively expressed at fairly low levels.

Another embodiment of the invention is directed to recombinant cells that contains a biotin-binding genetic containment system. The biotin-binding component may be the suicide gene product or a marker for the detection of recombinant cells. Useful cells may be prokaryotic or eukaryotic cells that require biotin or a derivative of biotin for viability, in the case of a suicide system, or any cell capable of expressing the biotin-binding component. Examples of useful eukaryotic cells include plant cells, insect cells, algae and mammalian cells. Examples of useful prokaryotic cells include gram-negative such as *E. coli*, and gram-positive cells such as *B. subtilis*, both of which are often utilized as GEMs. Recombinant cells may be unicellular such as with bacteria and yeast or multicellular such as with higher organisms provided that the recombinant cells of the multicellular organism can be identified. Optionally, cells may also express an inhibitor of the heterologous product as an additional control to prevent even minimal transcription occurring from the streptavidin gene. Preferably, the inhibitor is constituitively expressed at low levels by the cell so as not to interfere with induction of expression of the heterologous product.

Another embodiment of the invention is directed to coupling biotin-binding genetic cassettes to detection systems. This allows for the sensitive tracking of cells that, through natural or artificial means, express biotin, avidin or streptavidin. Environmental monitoring and detection of organisms based on the detection of streptavidin by biosensor-based systems is a major advantage such as, for example, to rapidly monitor cells using biotinylated lipid films as biosensors. In combination with biotinylated fluorescent probes, as little as ten microorganisms can be detected in a sample.

Another embodiment of the invention is directed to a method for selectively killing a recombinant microorganism. Utilizing the genetic containment systems described, a recombinant cell containing such a system can be selectively destroyed by activation of the suicide gene. Activation may be accomplished by the addition of extrinsic agents or higher or lower concentrations of intrinsic agents to the cellular environment. Upon recognition of the specific agent or agents, the cell self destructs according to its genetic programming.

Another embodiment of the invention is directed to a method for detecting a recombinant microorganism. A sample suspected of containing a cell containing a streptavidin-based genetic containment system is provided. The streptavidin-based containment system is comprised of a streptavidin gene placed under the control of a regulatable promoter regulated by a heterologous product expressed from an inducible promoter which can be induced by an extrinsic agent or a change in concentration of an intrinsic agent. The promoter is induced to express the heterologous product and activates transcription of the streptavidin gene.

The activated sample is contacted with a solid support to which is attached biotin. Cells which contain streptavidin become bound to the solid support and can be easily detected.

A streptavidin-based containment system can be used to control the survival of engineered microorganisms genetically constructed to degrade hazardous chemicals such as hydrocarbons, aromatic compounds and halogenated compounds including toluates, xylenes, benzenes, polycyclic hydrocarbons and derivatives and combinations of these compounds. According to the invention, microorganisms can be genetically altered to couple the control of degradation of different types of hazardous organic chemicals to the survival of the organism. This control is manifested in the self-destruction of the microorganism once the target chemicals in the environment have been degraded. This type of genetic control will function in laboratory or controlled fermentation settings, or in the field in actual bioremediation applications. The control of survival is based on expression of streptavidin protein which is only produced once the target chemical is degraded. Once there is no further target chemical present, or a critical lower threshold is reached, the gene encoding the streptavidin protein is expressed, and the organism is killed due to complexation of all the essential biotin vitamin in the cell with the newly expressed streptavidin. Aside from controlled fermentations and field remediation needs, this same containment or control system may be useful for the delivery of live vaccines and biopesticides, or a range of bioengineered products both in the field or in controlled laboratory environments.

Streptavidin-based containment systems of the invention are suitable for the treatment many types of contamination including toxic spills, sludge and activated sludge. The costs are expected to be less than half of the current technologies. Additional benefits for this approach are the noninvasive methods of treatment, the fact that no new potential contaminants will be added or left in the soil or water, and the process goes to completion for the target chemicals of interest. In addition, the proposed method is relatively simple and requires less engineering than conventional methods. As additional constructs are made, the scope of target chemicals that can be treated in this manner will increase.

Streptavidin-based genetic systems are also useful for environmental remediation. Both biological and non-biological treatments for contaminated soils and waters can be performed and at a lower effective cost. This same technology can also be used in biopesticide delivery or vaccine delivery as a way to control the organisms used in some of these processes. In addition, many suicide functions are being developed to control genetic elements such as viral and retroviral vectors, during gene therapy for medical treatments. The system described herein is adaptable for these applications as well. This technology can also be used to control cell lines involved in the production of important pharmaceuticals or drugs. It is often critical to control organisms in fermentation systems to assure that all organisms are killed after their useful life cycle in the production process. Should viable cells get out, carefully selected strains could be lost. Thus, the genetic containment system described may also be useful as a security system to provide enhanced assurance that there is no chance of release of viable organisms once growth is completed on a particular substrate.

The following experiments are offered to illustrate embodiments of the invention, and should not be viewed as limiting the scope of the invention.

EXAMPLES

Example 1 Bacterial Strains, Plasmids and Culture Conditions

Subcloning experiments were performed in *E. coli* DH5α (*recA1 hsdR17 endA1 thi-1 gyrA96 relA1 supE44φ80δlacZΔM15λ$^-$*) (T. Maniatis, *Molecular Cloning: A Laboratory Manual*, Cold Spring Harbor Laboratory, Cold Spring Harbor, N.Y., 1982). Suicide constructs were tested in the mentioned *E. coli* strain and *Pseudomonas putida* KT2440 (*hsdR1 hsdM$^+$*) (F. C. H. Franklin et al., Proc. Natl. Acad. Sci. USA 18:7458–62, 1981). DNA used were plasmids pKK223-3 (Amp$^r$) (J. Brosius et al., Proc. Natl. Acad. Sci. USA 6929–33, 1984), pLysE (Cm$_r$) (F. W. Studier et al., Methods Enzymol. 185:60–89, 1990), pRO1614 (Amp$^r$, Tet$^r$) (R. H. Olsen et al., J. Bacteriol. 150:60–69, 1982), pTSA-13 (Amp$^r$, pUC19 (Amp$^r$) (C. Yanisch-Peron et al., Gene 33:103–19, 1985), pVLT33 (Kan$^r$) (V. de Lorenzo et al., Gene 123:17–24, 1993), replicative form (rf) of bacteriophage mGP1-2, a derivative of pGP1-2 (S. Tabor et al., Proc. Natl. Acad. Sci. USA 82:1074–78, 1985), and synthetic oligonucleotides.

Bacteria were routinely grown at 30° C. in LB or M9/glucose medium supplemented with 1 mM thiamine for *E. coli*. Modified M9/glucose medium for *P. putida* was supplemented with A9 micronutrients (M.-A. Abril et al., J. Bacteriol. 171:6782–90, 1989). Antibiotics were used at the following concentrations: ampicillin and carbenicillin, 100 μg/ml (*E. coli*); kanamycin, 25 μg/ml (*E. coli*) or 75 μg/ml (*P. putida*); tetracycline, 10 μg/ml (*E. coli*). Isopropyl β-D-thiogalactopyranoside (IPTG) was used at a concentration of 1 mM.

DNA manipulations were carried out by standard procedures (T. Maniatis, *Molecular Cloning: A Laboratory Manual*, Cold Spring Harbor Laboratory, Cold Spring Harbor, N.Y., 1982). *P. putida* was transformed by a RbCl method (M. Bagdasarian et al., *Current Topics in Microbiology and Immunology*, Springer-Verlag, P. M. Hofschneider and W. Goebel editors, 1982) or by electroporation (effidency~$10^7$ transformants/μg DNA on Gene Pulser apparatus with Pulse Controller, Bio-Rad, set at 25 μF, 2.50 kV, and 200 Ω for a 0.2 cm cuvette).

Example 2 Design of a Lethal Cassette

To employ streptavidin as a suicide component in biological containment system, the stv gene can be fused with the regulated promoter $P_{lac}$ or its derivatives, $P_{UV5}$, $P_{tac}$, etc. Transcription of the stv gene could be repressed by *E. coli* LacI protein synthesized upon environmental induction. A potential drawback of such a design is an insufficient repression of most of $P_{lac}$ type promoters by LacI protein. Together with high toxicity of streptavidin, this will cause failure of the whole system due to accumulation of mutants, or poor killing efficiency in case of huge overproduction of LacI repressor.

To achieve tighter control of streptavidin synthesis, the stv gene was placed under the regulation of the bacteriophage T7 expression system (T. Sano et al., Proc. Natl. Acad. Sci. USA 87:142–46, 1990). In this case, transcription of the stv gene is controlled by the T7 φ10 promoter which is recognized only by T7 RNA polymerase. Bacteriophage polymerase is provided from the T7 gene 1, placed under control of the $P_{tac}$ promoter, negatively regulated by the LacI repressor. To compensate for the leakiness of $P_{tac}$, an inhibitor of T7 RNA polymerase, T7 lysozyme (B. A. Moffatt et al., Cell 49:221–27, 1987), was also supplied. It was expressed from the T7 gene 3.5 placed under the *P. putida* TOL plasmid $P_m$ promoter. In an uninduced state in *E. coli*, $P_m$ behaves as a very weak constitutive promoter, allowing sufficient synthesis of T7 lysozyme to inactivate low levels of T7 RNA polymerase. The $P_m$ promoter was chosen because leaving the lysozyme gene even without promoter appeared to be sufficient to reduce leakiness of $P_{tac}$. Higher levels of lysozyme in the system are designed to respond to low levels $P_m$ promoter activator which completely represses basal T7 RNA polymerase expression. Streptavidin is expressed upon inactivation of LacI with IPTG, or, if the lacI gene is fused to, for example, the $P_m$ promoter, in response to depletion of a hydrocarbon effector.

With this design, lethal expression of the stv gene is tightly controlled by the bacteriophage T7 transcription system, that is the φ10 promoter, the RNA polymerase encoded by the T7 gene 1 fused with Escherichia coli $P_{tac}$ promoter, and the lysozyme, here as an inhibitor of RNA polymerase. This entire containment system can be conditioned by the E. coli lacI repressor gene fused with a promoter responding to environmental or physiological changes. A plasmid-based construct was examined in E. coli and Pseudomonas putida. Induction of stv gene expression resulted in cell-killing with efficiency up to 99.9%. Mutants escaping killing appeared at frequencies reaching $10^{-6}$–$10^{-7}$ per cell per generation. The general requirement for biotin in the living systems makes the stv cassette a candidate for containment strategies in a broad range of microorganisms.

Example 3 Construction of a Streptavidin System $P_{tac}$:: T7 gene 1 fusion: The T7 RNA polymerase gene was derived from mGP1-2 rf DNA by cleavage with EcoR I and Pst I, and subcloned into the EcoR I and Pst I sites of pKK223-3.

$P_m$:: T7 gene 3.5 fusion: A P. putida TOL meta-cleavage pathway $P_m$ promoter region (B. Kessler et al., J. Mol. Biol. 230:699–703, 1993) was assembled from two complementary 110-base oligonucleotides designed to have EcoR I and Sac I ends after annealing. It was inserted into the EcoR I and Sac I sites of pUC19. The T7 lysozyme gene was cut out from pLysE with BamH I, blunt-ended with Klenow polymerase, and inserted into the Sma I site of the pUC19 derivative, downstream from $P_m$.

T7 gene 3.5—stv gene cluster: The pUC19 derivative bearing the T7 lysozyme gene was cut with BamH I, blunt-ended with Klenow polymerase, and then cut with EcoR I. A fragment containing the lysozyme gene fused the $P_m$ promoter was inserted into the EcoR I and EcoR V sites of pTSA-13, a pET-3a derivative with the stv gene encoding the core streptavidin (amino acids 16-133 of the mature protein) under the control of the T7 φ10 promoter.

stv gene—T7 gene 3.5—T7 gene 1 cassette: A fragment of a pTSA-13 derivative containing the T7 lysozyme and stv genes with their regulatory sequences was cut out with EcoR I and Bgl II, and blunt-ended with Klenow polymerase. This blunt-ended fragment was inserted into the blunt-ended BamH I site of the pKK derivative described above, upstream from the $P_{tac}$:: T7 gene 1 fusion. A Sph I-Hind III fragment of the resulting plasmid pKK-slp bearing the stv cassette (FIG. 1) was finally inserted into the Sph I and Hind III sites of pRO1614, a vector for enteric bacteria and pseudomonads.

Example 4 Functionality Tests of stv Gene-based Constructs

Figure 2:
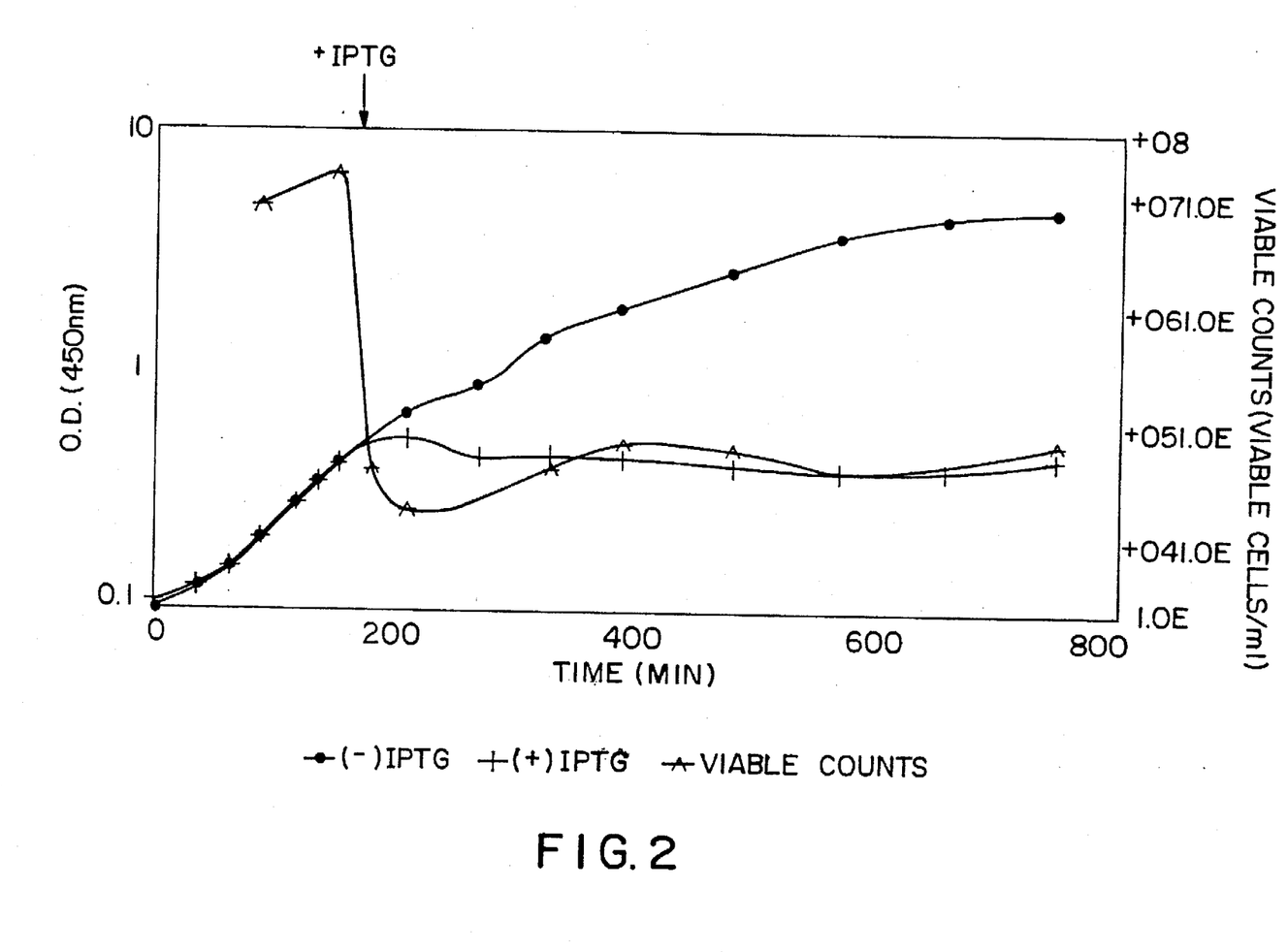
FIG. 2 IPTG-induced in vitro containment of *E. coli* DH5α (pRO-slp). Cultures were grown in the presence of ampicillin.
Figure 3:
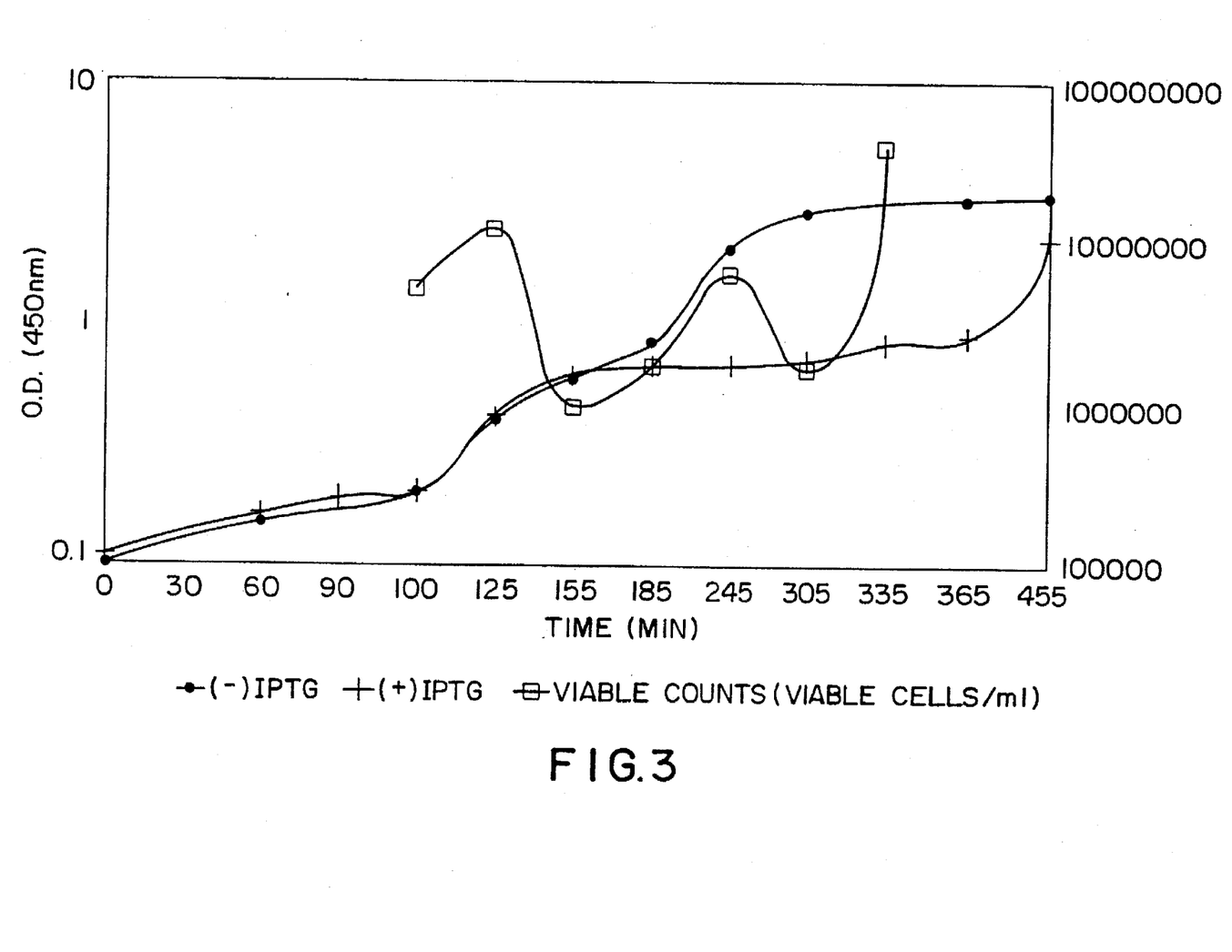
FIG. 3 IPTG-induced in vitro containment of *P. putida* KT2440 (pVLT-slp). Cultures were grown in the presence of kanamycin.

Functionality of the stv gene-based design was analyzed in E. coli by constructing a DH5α strain carrying plasmids pKK-slp or pRO-slp. P. putida, which does not contain the lacI gene on the chromosome, was first transformed with pVLT33 (lacA) and then with pRO-slp. However, in P. putida such construct did not respond to IPTG, probably because of overproduction of LacI. Similar behavior of P. putida has been already reported. To be able to check the stv cassette in P. putida, it was inserted into a multiple cloning site of a pVLT33 derivative with lacI gene depleted from its own promoter. In this case (pVLT-lslp) transcription of lacI was very low, originating somewhere within the stv cassette. Cultures were grown overnight in LB medium supplemented with appropriate antibiotic, diluted with the same medium to $A_{450nm}$~0.1, and further grown to early exponential phase. As shown in FIGS. 2 and 3, the addition of IPTG at $A_{450}$~0.4 inhibited cell growth, both in E. coli and P. putida.

Example 5 Efficiency of Streptavidin Killing Function

Luria-Delbrüuck experiments (S. E. Luria et al., Genetics 28:491–511, 1943) were performed using 96-well microtiter plates and carbenicillin instead of ampicillin (L. B. Jensen et al., Appl. Environ. Microbiol. 59:3713–17, 1993). The efficiency of killing of host cells by the expression of streptavidin was tested by counting viable cells before addition of IPTG, and at different times after. Bacterial samples were washed with LB medium to remove IPTG, spread on LB agar plates supplemented with appropriate antibiotic and 50 μg/ml biotin, and incubated for a week. An hour after induction of streptavidin synthesis, 99.9% of E. coli and 92.3% of P. putida cells could not recover even after prolonged incubation in the presence of biotin (FIG. 3). Surviving colonies of E. coli contained a fully active suicide system, as checked on plates with and without IPTG. A progressive growth up of bacterial population after about 10 hours of exposure to IPTG resulted from the loss of the plasmid due to destruction of ampicillin by β-lactamase released to the medium. In case of P. putida, all surviving clones appeared to contain mutations (probably point mutations) within the suicide system. That is why in this case cultures resumed just 3 hours after induction of the stv gene. Rates of mutational inactivation of the streptavidin-based suicide system in E. coli DH5α and P. putida KT2440 are shown in Table 1.

TABLE 1

Fluctuation Test Results

| Strain | Mutation Rates of stv Constructs |
| --- | --- |
| E. coli DH5α (pRO-slp) | $3.2 \times 10^{-6}$ |
| E. coli DH5α (pVLT33, pRO-slp) | $2.1 \times 10^{-7}$ |
| P. putida KT2440 (pVLT01slp) | $2.0 \times 10^{-4}$ |

Mutation rates in E. coli were comparable to those published for other constructs with a single toxic gene. The higher rate observed for P. putida is apparently due to an insufficient repression of the $P_{tac}$ promoter in the uninduced state on account of a very low level of LacI synthesis.

Other embodiments and uses of the invention will be apparent to those skilled in the art from consideration of the specification and practice of the invention disclosed herein. The specification and examples should be considered exemplary only with the true scope and spirit of the invention indicated by the following claims.

We claim:

1. A method for selectively killing a recombinant organism comprising the steps of:
   a) providing a cell that contains a suicide cassette comprised of a suicide gene that encodes a biotin-binding protein functionally linked to a promoter whose activity is regulated by a transcriptional effector; and
   b) stimulating said transcriptional effector.

2. The method of claim 1 wherein the cell is a genetically engineered microorganism.

3. The method of claim 2 wherein the genetically engineered microorganism is used for bioremediation.

4. The method of claim 1 wherein the biotin-binding protein is streptavidin or avidin.

5. The method of claim 1 wherein the promoter is a T7 promoter and the transcriptional effector is a T7 RNA polymerase.

6. The method of claim 1 wherein the promoter is a *lac* promoter or part thereof.

7. The method of claim 1 wherein the addition of an extrinsic agent stimulates transcription from said transcriptional effector or inactivates a transcriptional repressor of said transcriptional effector.

8. The method of claim 7 wherein the extrinsic agent is IPTG or an analog thereof.

9. The method of claim 1 wherein the cell constituitively expresses an inhibitor of the transcriptional effector.

10. A method for selectively killing a recombinant organism comprising the steps of:

a) providing a cell that contains a cassette comprised of a suicide gene that encodes a biotin-binding protein functionally linked to an inducible promoter, a suicide control gene encoding a heterologous polymerase functionally linked to a repressible promoter regulated by a repressor, and a polymerase control gene functionally linked to a constitutive promoter; and b) stimulating said inducible promoter.

11. The method of claim 10 wherein the suicide gene encodes streptavidin, avidin mutants thereof.

12. The method of claim 10 wherein the inducible promoter is a bacteriophage λ, SP6, T3 or T7 promoter.

13. The method of claim 10 wherein the heterologous polymerase is a bacteriophage, SP6, T3 or T7 polymerase.

14. The method of claim 10 wherein the repressor is a lactose, galactose or tryptophan repressor protein.

15. The method of claim 10 wherein the repressible promoter is $P_{tac}$, $P_{lac}$, $P_{trp}$, $P_{gal}$ or $P_{phoA}$.

16. The method of claim 10 wherein the polymerase control gene encodes a lysozyme.

17. The method of claim 10 wherein the constitutive promoter is $P_m$.

18. The method of claim 10 further comprising a gene encoding the repressor protein that is functionally linked to a second inducible promoter.

19. The method of claim 18 wherein said second inducible promoter is activated or repressed in response to a change of an environmental condition.

20. The method of claim 19 wherein the environmental condition is the change in concentration of a chemical, metal, radiation or nutrient or change in pH.

21. A method for selectively killing a recombinant organism comprising the steps of:

a) providing a cell that contains a cassette comprised of a suicide gene encoding a biotin-binding protein functionally linked to an inducible promoter, a suicide control gene encoding a polymerase functionally linked to a repressible promoter, a polymerase control gene functionally linked to a constitutive promoter, and a gene that encodes said repressor functionally linked to second inducible promoter that responds to an environmental condition; and b) stimulating said inducible promoter.

* * * * *